United States Patent
VanMetter et al.

(10) Patent No.: US 7,623,628 B2
(45) Date of Patent: Nov. 24, 2009

(54) CARDIAC GATING FOR DUAL-ENERGY IMAGING

(75) Inventors: Richard L. VanMetter, Washington, DC (US); Jeffrey H. Siewerdsen, Toronto (CA); Nick A. Shkumat, Houston, TX (US); John Yorkston, Penfield, NY (US)

(73) Assignee: Carestream Health, Inc., Rochester, NY (US)

( * ) Notice: Subject to any disclaimer, the term of this patent is extended or adjusted under 35 U.S.C. 154(b) by 9 days.

(21) Appl. No.: 11/951,483

(22) Filed: Dec. 6, 2007

(65) Prior Publication Data

US 2008/0198964 A1 Aug. 21, 2008

Related U.S. Application Data

(60) Provisional application No. 60/869,163, filed on Dec. 8, 2006, provisional application No. 60/889,365, filed on Feb. 12, 2007.

(51) Int. Cl.
*A61B 6/00* (2006.01)
(52) U.S. Cl. ...................................................... 378/95
(58) Field of Classification Search .................. 378/8, 378/95; 600/428
See application file for complete search history.

(56) References Cited

U.S. PATENT DOCUMENTS 6,154,516 A * 11/2000 Heuscher et al. .............. 378/15
6,816,572 B2 11/2004 Jabri et al.

OTHER PUBLICATIONS

Siewerdsen et al., "High-Performance Dual-Energy Imaging with a Flat-Panel Detector: Imaging Physics from Blackboard to Benchtop to Bedside," Medical Imaging 2006: Physics of Medical Imaging, Proceedings of the SPIE, vol. 6142, (Mar. 2006), pp. 489-498.*

* cited by examiner

*Primary Examiner*—Chih-Cheng G Kao

(57) ABSTRACT

Methods are provided for cardiac gating of multiple-energy projection radiographic imaging utilizing an apparatus that measures the patient's peripheral blood perfusion. The choice of methods is dependant on the patient's heart rate and the delays inherent in the imaging system. A first method allows for imaging during the diastole period of the current cardiac cycle. A second method provides an implemented delay to acquire the image during the diastole period of a subsequent cardiac cycle. The use of the apparatus that measures the patient's peripheral blood perfusion allows for an efficient and convenient means of cardiac gating while avoiding occlusion of diagnostically important anatomy.

18 Claims, 4 Drawing Sheets

CARDIAC GATING FOR DUAL-ENERGY IMAGING

CROSS REFERENCE TO RELATED APPLICATIONS

This application claims the priority benefit of U.S. Provisional Applications No. 60/869,163 titled HIGH PERFORMANCE DUAL-ENERGY IMAGING WITH A FLAT-PANEL DETECTOR: IMAGING PHYSICAL FROM BLACKBOARD TO BENCHTOP TO BEDSIDE filed Dec. 8, 2006 in the names of VanMetter et al. and U.S. Provisional Applications No. 60/889,365 titled DEVELOPMENT AND IMPLEMENTATION OF A HIGH-PERFORMANCE CARDIAC-GATED DUAL-ENERGY IMAGING SYSTEM filed Feb. 12, 2007 in the names of VanMetter et al, both of which are incorporated herein by reference.

FIELD OF THE INVENTION

The invention relates generally to the field of projection radiography and in particular to the acquisition of multiple-energy projection radiographic images. More specifically, the invention relates to a method of cardiac gating for multiple-energy imaging that mitigates artifacts resulting from cardiac motion.

BACKGROUND OF THE INVENTION

In multiple-energy projection radiographic imaging, a number of images of the same object are acquired that reveal the x-ray transmittance of the object for differing x-ray spectra. The images are acquired sequentially through the use of an x-ray detector. The images can be decomposed to produce material specific images, such as tissue-only and bone-only images.

Radiographic imaging procedures that require multiple exposures, such as dual-energy imaging, acquire multiple images over a period of time, which may include different stages of the cardiac cycle. The different stages of the cardiac cycle are associated with motion of the heart and the arterial vessels. As such, the relative anatomical motion of the heart and the arterial vessels between the acquired images gives rise to artifacts in the reconstructed image. Anatomical motion and the resulting artifacts can be avoided by timing the image acquisition to occur only during a particular stage of the cardiac cycle, for example diastole when heart motion is minimal. This is commonly referred to as "cardiac gating".

Electro-cardio-graph (ECG) signals have been used as a method of cardiac gating. ECG, however, requires that electrical contact be made to the patient's skin by means of adhesive pads with attached electronic wires. The electrical contacts are normally attached to areas of the chest. The conductive pads are radio-opaque and can occlude diagnostically important areas of the patient's anatomy. The use of ECG for cardiac gating also requires time consuming preparation of the attachment site, uncomfortable removal of the conductive pads, and the expense and inconvenience of disposable contact pads.

Therefore, there is a need to provide a more convenient and efficient method of cardiac gating for dual-energy imaging that will not occlude the x-ray beam.

SUMMARY OF THE INVENTION

The present invention provides alternative methods of cardiac gating for projection radiographic imaging. Both methods comprise measuring the duration of the patient's cardiac cycle. The measurement of the duration of the patient's cardiac cycle can be performed using an apparatus that measures peripheral blood perfusion, such as a pulse oximeter. A pulse oximeter reports the percentage of arterial oxygen, computed through absorption characteristics of oxygenated hemoglobin and deoxygenated hemoglobin. The duration of the patient's cardiac cycle can be averaged over a fixed number of cycles to estimate the patient's instantaneous heart rate.

The cardiac cycle can be reduced into two distinct mechanical periods: diastole and systole. As the patient's heart rate changes, the proportion of time that the heart spends within each phase is affected. Lasting for approximately 0.6 seconds in an average person having a heart rate of 67 beats per minute, diastole encompasses the quiescent phase of the heart where blood flows passively from the atria into the ventricles. Systole lasts approximately 0.3 seconds in an average person and is the largest contributor to cardiac motion within the cardiac cycle.

Both methods include determining whether the duration of patient's cardiac cycle provides adequate time to acquire the image during the diastole region of the current cardiac cycle. The determination of whether there is adequate time to acquire the image during the diastole region of the current cardiac cycle is dependent on the duration of the patient's cardiac cycle, physiological and system-component delays in the pulse oximeter, and the maximum delay in the imaging system.

In the event that the duration of the patient's cardiac cycle is sufficient, one example method includes triggering the imaging system to acquire the image during the diastole region of the current cardiac cycle. In the event that the duration of the patient's cardiac cycle does not meet the threshold requirement, a second example method includes implementing a delay that delays acquisition into the diastole period of the subsequent cardiac cycle. The delay can be implemented utilizing either hardware or software. The second method further includes triggering the imaging system to acquire the image during the subsequent diastole region of the patient's cardiac cycle.

Both methods can be designed to acquire images at a fixed point during the diastole period of the patient's cardiac cycle, such as the mid-point of the cardiac cycle. Both methods can be further designed to acquire images during a specific sub-phase of the diastole period.

The present invention provides a method of cardiac gating for multiple-energy imaging that allows for accurate image acquisition during the diastole period of the cardiac cycle while avoiding occlusion of diagnostically important areas of the anatomy. The present invention also provides a more convenient and efficient means of acquiring cardiac cycle information for use in cardiac gating.

BRIEF DESCRIPTION OF THE DRAWINGS

The foregoing and other objects, features, and advantages of the invention will be apparent from the following more particular description of the embodiments of the invention.

DETAILED DESCRIPTION OF THE INVENTION

In the following description dual-energy imaging is described to illustrate an embodiment of the present invention. The present invention may also be applied to the acquisition of multiple-energy projection radiographic images. Each projection radiographic image of the multiple-energy projection radiographic images may be of the same or different energy level. For example, when three projection radiographic images are generated two projection radiographic images may be of the same energy level and the third projection radiographic image may be of a different energy level. Also, the use of a pulse oximeter is described to illustrate an embodiment of the invention. The present invention may also be performed using alternative devices that measure peripheral blood perfusion.

Figure 1:
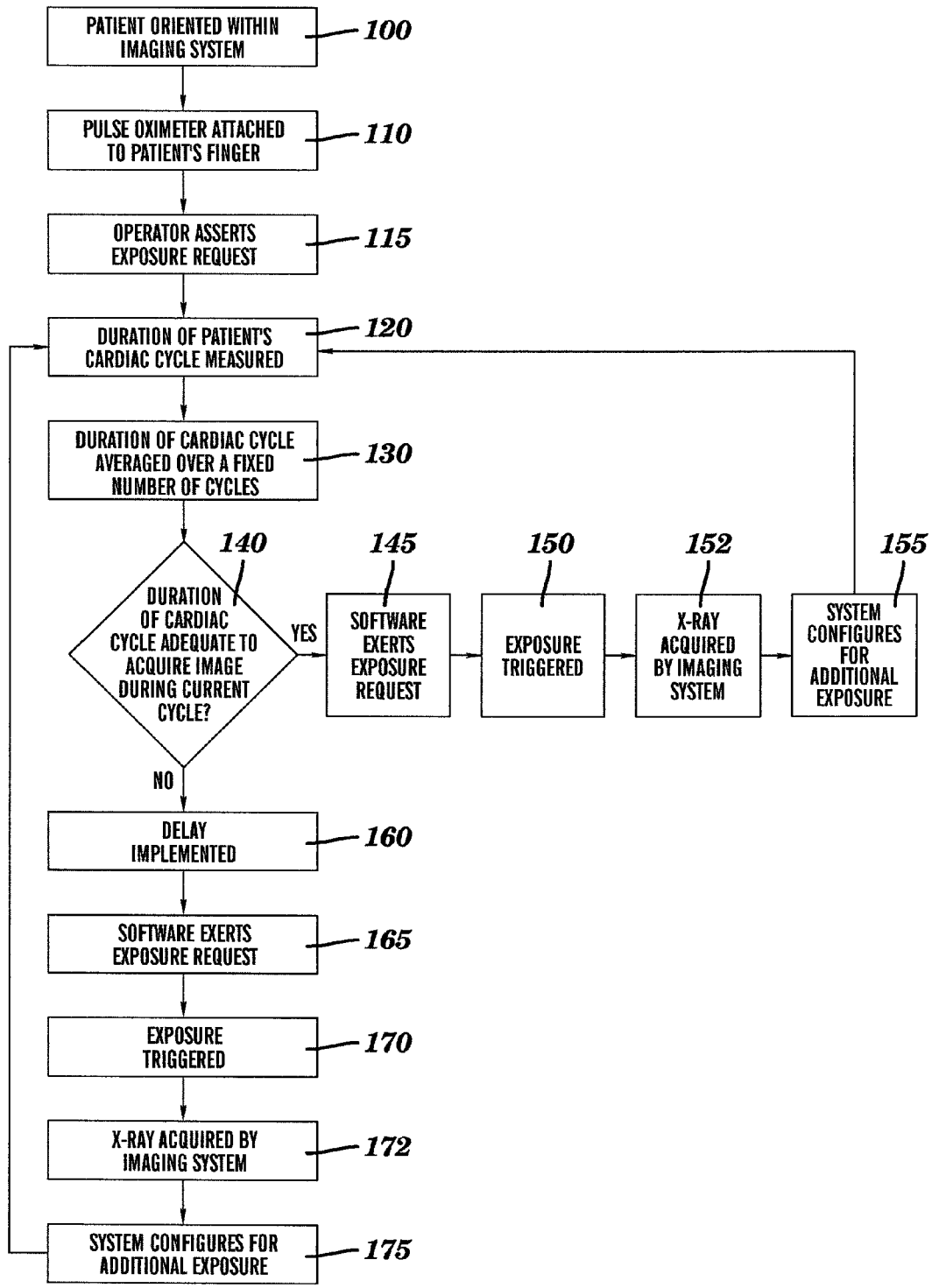
FIG. 1 shows a logic flow diagram illustrating a method of cardiac gating for multiple-energy imaging in accordance with an embodiment of the present invention.

Referring now to FIG. 1, a logic flow diagram illustrating a method of cardiac gating for dual-energy projection radiographic image acquisition in accordance with an embodiment of the present invention is shown.

In step 100, a patient is oriented within the imaging system. In step 110, a pulse oximeter is attached to the patient's finger. In step 115 the operator asserts a request to acquire an x-ray exposure.

In step 120, the duration of the patient's cardiac cycle is measured using the pulse oximeter. The pulse oximeter features signal processing firmware that generates both an oximeter signal (plethysmogram) as well as a digital trigger pulse. Although the pulse oximeter does not directly measure heart movement, the oximeter can be calibrated to effectively determine the duration and location within the cardiac phase. In order to calibrate the oximeter physiological and system component delays must be quantified. The most important and largest delay is the time required for blood propagation through the patient's vasculature, for example from the left ventricle to the left index finger. This temporal delay, combined with delays associated with internal processing of the oximeter itself, offsets the plethysmogram and the digital trigger from the true motion of the heart.

Figure 2:
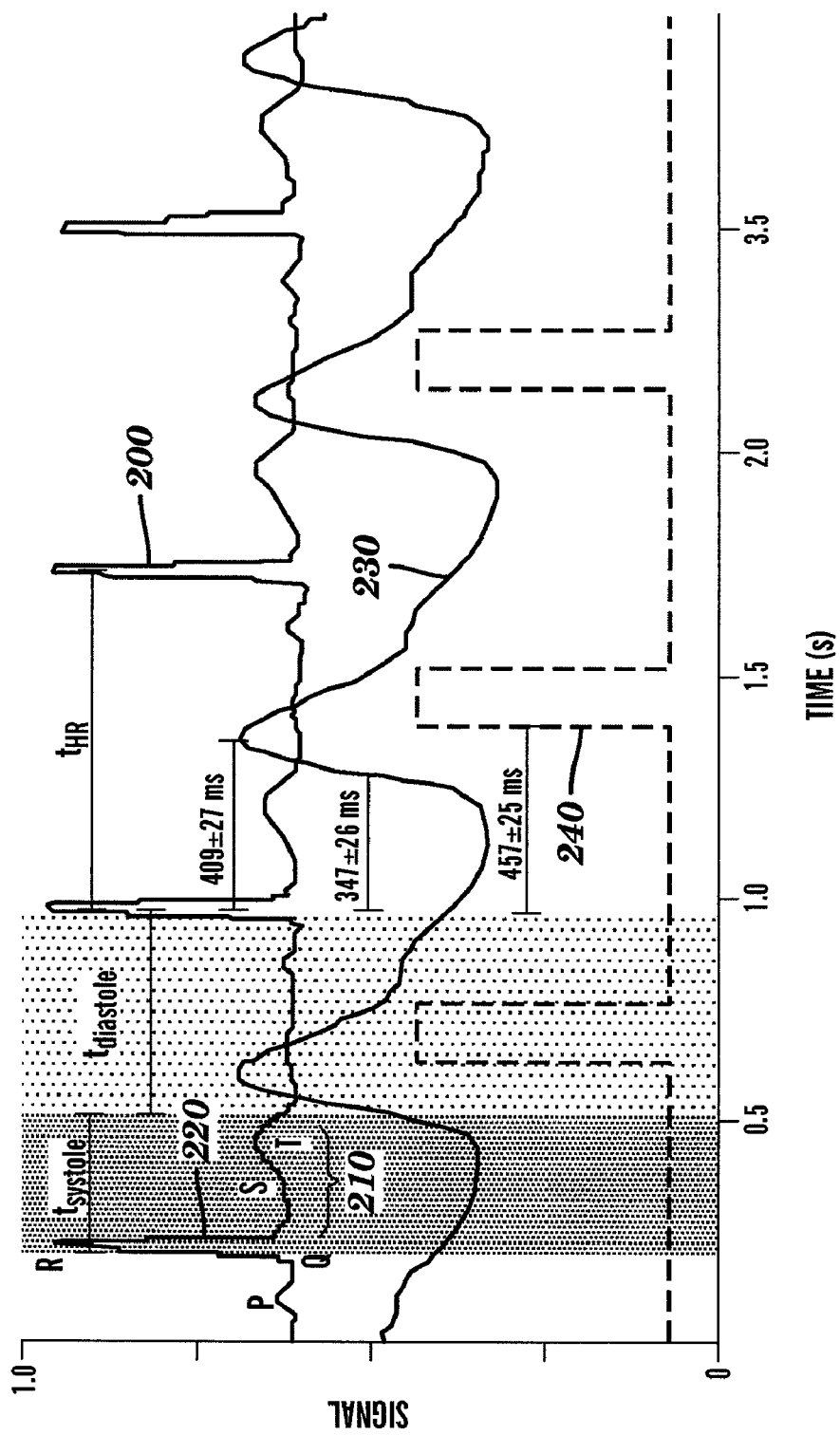
FIG. 2 shows a sample graph displaying the signal results for a patient monitored simultaneously using an ECG and a pulse oximeter.

The pulse oximeter can be calibrated to predict heart motion by monitoring a patient's heart rate simultaneously using an ECG and a pulse oximeter. Calibration of the pulse oximeter will now be described with reference to FIG. 2. FIG. 2 depicts a sample graph displaying the signal results for a patient monitored simultaneously using an ECG and a pulse oximeter. In the ECG trace 200 the QT interval 210 is defined as systole. The QRS complex 220 can be used to predict the start of systole. The delay between the QRS complex 220 and various temporal landmarks in the plethysmogram 230 can be determined. The delay between the QRS complex 220 and the digital trigger 240 can also be determined. These delays have been found to be stable across both heart-rate and age. The delay between the ECG signal and the mechanical event of the start of systole must also be taken into account to determine the true delay between the start of systole and the digital trigger. This delay is physiological and has been experimentally determined to be approximately 50 ms.

Referring again to FIG. 1, in step 130, the duration of the patient's cardiac cycle, as determined by the plethysmogram, is averaged over a fixed number of cycles to estimate the patient's instantaneous heart rate. The proportion of the time that the heart spends within each phase of the cardiac cycle is affected by the patient's heart rate. Knowledge of the patient's heart rate and an indicator of the relative timing position within the cycle allow for predictions of the duration of diastole and the time at which the subsequent systole will end, thereby providing an accurate indicator of when the subsequent diastole period will begin.

In step 140, a determination is made whether the duration of patient's cardiac cycle provides adequate time to acquire the image during the diastole region of the current cardiac cycle. The determination of whether there is adequate time to acquire the image during the diastole region of the current cardiac cycle is dependent on the duration of the patient's cardiac cycle, the delay between the start of systole and the digital trigger and the maximum delay in the imaging system.

Imaging systems are affected by internal delays, inherent in each individual imaging system, which act in combination and can influence the timing of image acquisition relative to an arbitrary timing signal, such as the beginning of the diastole period. The imaging system delays can be divided into two categories; delays that affect single image acquisition and delays that occur between dual-energy exposures. Examples of intra-exposure delays include: the time required for the software to assert a request for exposure after an input timing signal is provided, the time required for grid motion to begin and be confirmed after a software request for grid motion is asserted, the time required for the detector to assert an exposure request to the x-ray generator after it receives a software request for exposure, and the time required for the generator to produce an x-ray pulse after it has been requested by the detector. Examples of inter-exposure delays include: the time required for the generator to switch energy levels after a software request is asserted, the time required for the filter wheel to rotate after a software request is asserted, and the time required to transfer image data from the previous exposure from the detector to temporary storage and for the detector to be in a ready state, capable of responding to a software request for exposure.

The delays in the imaging system can be characterized by a fixed component and a variable component. These delays are inherent in the imaging system. The maximum and minimum delays of the imaging system, $t^{max}_{FPD}$ and $t^{min}_{FPD}$, respectively, can be experimentally determined.

Given the delays in both the cardiac cycle monitoring using a pulse oximeter and the imaging system, correct timing of the x-ray exposure can be assured by using selectively implemented delays in either software or hardware. Both the timing and the duration that the heart spends in diastole are dependent upon the patient's heart rate. Assuring that the x-ray exposure falls within the limits of the diastole period is an important problem, which is confounded by the interdependent delays caused by each of the system components. These considerations make it necessary to provide two methods to trigger a cardiac gated exposure: within the diastole region of the current cardiac cycle or within the diastole region of a subsequent cardiac cycle. While it is always desirable to trigger each acquisition with the current diastole, the length and variability of the delays inherent in the imaging system can preclude that option.

There is adequate time to acquire the image during the diastole period of the current cardiac cycle if the following inequality is satisfied:

$$[t_{HR}(HR) - t_{trigger}] > [t^{max}_{FPD} + t_{buffer}]$$

wherein $t_{HR}(HR)$ represents the duration of the patient's cardiac cycle, $t_{trigger}$ represents the delay between the start of systole and the digital trigger, $t^{max}_{FPD}$ represents the maximum delay in the imaging system and $t_{buffer}$ represents a buffer period used to account for x-ray duration and a designed safety margin.

Figure 3:
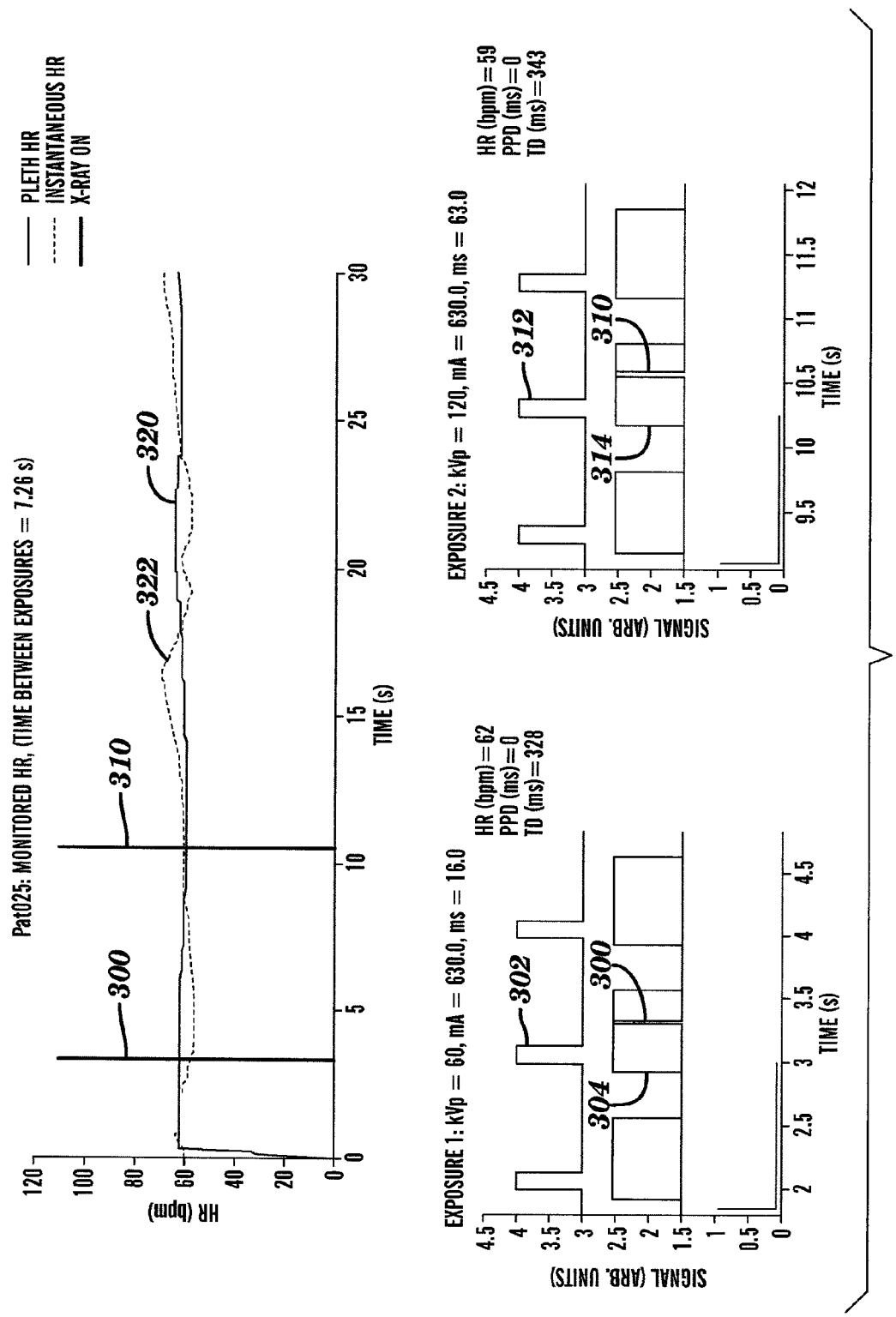
FIG. 3 shows experimental results for a dual-energy exposure where both the first exposure and the second exposure are triggered during the current diastole period.

As indicated in decision block 140, if the inequality is satisfied the software asserts an exposure request in step 145. In step 150 the exposure is triggered during the diastole period of the current cardiac cycle. In step 152 the x-ray is acquired by the imaging system. In step 155 the system configures itself to obtain additional exposures. The process is then repeated from step 120 to acquire additional exposures. FIG. 3 depicts experimental results for a dual-energy exposure where both the first exposure 300 and the second exposure 310 are triggered in response to digital triggers 302 and 312, respectively. The patient's heart rate 320, as measured by the plethysmogram, provides adequate time to trigger the x-ray exposure during the diastole period of the current cardiac cycle based upon the delays inherent in the oximeter and the imaging system. As such, both exposures are triggered during diastole periods 304 and 314, which occur during the current cardiac cycle. The patient's instantaneous heart rate 322 is determined by averaging the plethysmogram measured heart rate 320 over several cardiac cycles.

Referring again to FIG. 1, if the inequality is not satisfied, a delay is implemented in step 160 to acquire the image in the diastole period of the subsequent cardiac cycle. The implemented delay is provided by the following equation:

$$t_{imp} = [t_{HR}(HR) - t_{trigger}] + [t_{systole}(HR) - t^{min}_{FPD}] + x[t_{diastole}(HR) - (t^{max}_{FPD} - t^{min}_{FPD})]$$

wherein $t_{imp}$ is the required implemented delay, $t_{HR}(HR)$ represents the duration of the patient's cardiac cycle, $t_{trigger}$ represents the delay between the start of systole and the digital trigger, $t_{systole}(HR)$ and $t_{diastole}(HR)$ represent the duration of systole and diastole, respectively, and $t^{max}_{FPD}$ and $t^{min}_{FPD}$ are the maximum and minimum delay of the system, respectively. The x term represents a variable that is used to determine a fixed-point in the diastole period in which the exposure is obtained. For example, for x=½ the exposure is acquired at the mid-point of the diastole period. The variable term can be adjusted to acquire the image at a specific sub-phase of the diastole period.

Figure 4:
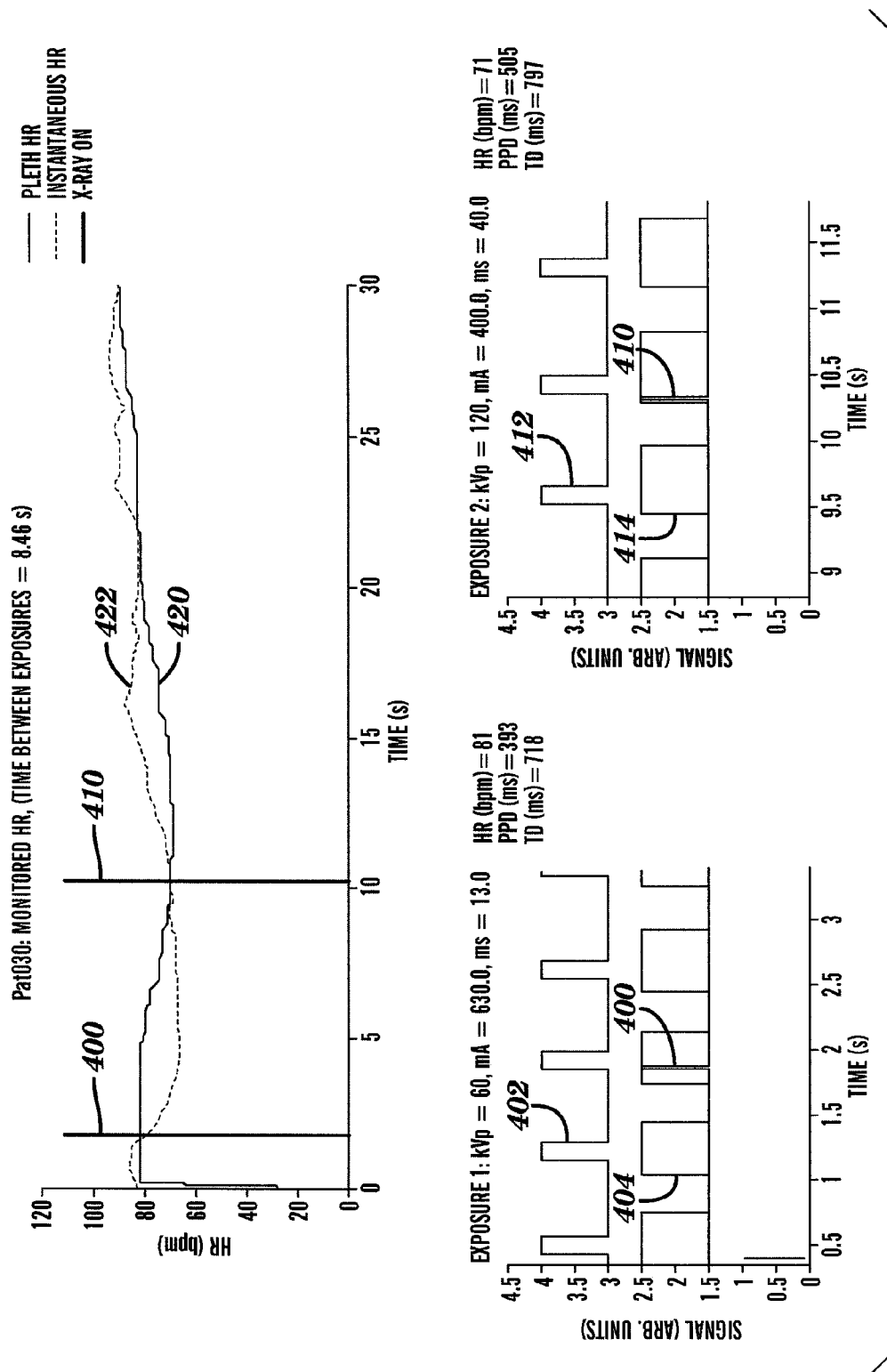
FIG. 4 shows experimental results for a dual-energy exposure where both the first exposure and the second exposure are triggered following an implemented delay during a subsequent diastole period.

In step 165 the software asserts an exposure request. In step 170, the exposure is triggered during the diastole period of the subsequent cardiac cycle. In step 172 the x-ray is acquired by the imaging system. In step 175 the system configures itself to obtain additional exposures. The method is then repeated from step 120 to acquire additional exposures. FIG. 4 depicts experimental results for a dual-energy exposure where both the first exposure 400 and the second exposure 410 are triggered in response to digital triggers 402 and 412, respectively. The patient's heart rate 420, as measured by the plethysmogram, did not provide adequate time to trigger the x-ray exposure during the diastole period of the current cardiac cycle based upon the delays inherent in the oximeter and the imaging system. As such, a delay was implemented such that both exposures are triggered during diastole periods 404 and 414, which occur during the subsequent current cardiac cycle. The patient's instantaneous heart rate 422 is determined by averaging the plethysmogram measured heart rate 420 over several cardiac cycles.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method of cardiac gating for projection radiographic imaging comprising:
    measuring the duration of the patient's cardiac cycle using an apparatus designed to measure peripheral blood perfusion;
    determining whether the duration of patient's cardiac cycle provides adequate time to acquire the image during the diastole region of the current cardiac cycle; and
    triggering the imaging system to acquire the image during the diastole region of the current cardiac cycle in the event that there is adequate time.

2. The method of claim 1 wherein the apparatus is a pulse oximeter.

3. The method of claim 1 wherein the duration of the patient's cardiac cycle is averaged over a fixed number of cycles to estimate the patient's instantaneous heart rate.

4. The method of claim 1 wherein determining whether there is adequate time to acquire the image during the diastole region of the current cardiac cycle is dependent on the duration of the patient's cardiac cycle, the delay in the measuring apparatus, the maximum delay in the imaging system and a buffer period.

5. The method of claim 1 wherein determining whether there is adequate time to acquire the image during the diastole region of the current cardiac cycle includes determining if the following inequality is satisfied:

$$[t_{HR}(HR) - t_{trigger}] > [t^{max}_{FPD} + t_{buffer}];$$

wherein: $t_{HR}(HR)$ is the duration of the patient's cardiac cycle; $t_{trigger}$ is the delay in the measuring apparatus; $t^{max}_{FPD}$ is the maximum delay in the imaging system; and $t_{buffer}$ is a buffer period used to account for x-ray duration and a designed safety margin.

6. The method of claim 1 wherein the image is acquired during a fixed point of the diastole period of the cardiac cycle.

7. The method of claim 6 wherein the fixed point of the diastole period of the cardiac cycle is the mid-point of the diastole period.

8. The method of claim 1 wherein the image is acquired in a specific sub-phase of the diastole period of the cardiac cycle.

9. A method for cardiac gating for projection radiographic imaging comprising:
    measuring the duration of the patient's cardiac cycle using an apparatus designed to measure peripheral blood perfusion;
    determining whether the duration of patient's cardiac cycle provides adequate time to acquire the image during the diastole period of the current cardiac cycle;
    implementing a delay; and
    triggering the imaging system to acquire the image during a subsequent diastole region of the patient's cardiac cycle.

10. The method of claim 9 wherein the apparatus is a pulse oximeter.

11. The method of claim 9 wherein the duration of the patient's cardiac cycle is averaged over a fixed number of cycles to estimate the patient's instantaneous heart rate.

12. The method of claim 9 wherein the determination of whether there is adequate time to acquire the image during the diastole region of the current cardiac cycle is dependent on the duration of the patient's cardiac cycle, the delay in the measuring apparatus, the maximum delay in the imaging system and a buffer period.

13. The method of claim 9 wherein there is adequate time to acquire the image during the diastole period of the current cardiac cycle if the following inequality is satisfied:

$$[t_{HR}(HR) - t_{trigger}] > [t^{max}_{FPD} + t_{buffer}];$$

wherein: $t_{HR}(HR)$ is the duration of the patient's cardiac cycle; $t_{trigger}$ is the delay in the measuring apparatus: $t^{max}_{FPD}$ is the maximum delay in the imaging system; and $t_{buffer}$ is a buffer period used to account for x-ray duration and a designed safety margin.

14. The method of claim 9 wherein the implemented delay depends on the patient's instantaneous heart rate, the fixed timing delays of the imaging system and the variable timing delays of the imaging system.

15. The method of claim 9 wherein the implemented delay is determined by the following equation:

$$t_{imp} = [t_{HR}(HR) - t_{trigger}] + [t_{systole}(HR) - t^{min}_{FPD}] + x[t_{diastole}(HR) - (t^{max}_{FPD} - t^{min}_{FPD})]$$

wherein: $t_{imp}$ is the required implemented delay: $t_{HR}(HR)$ is the duration of the patient's cardiac cycle; $t_{trigger}$ is the delay in the measuring apparatus; $t_{systole}(HR)$ is the duration of the systole; $t^{min}_{FPD}$ is the minimum delay of the system; x is a variable used to determine a fixed point in the diastole period in which the exposure is obtained; $t_{diastole}(HR)$ is the duration of the diastole; and $t^{max}_{FPD}$ is the maximum delay of the system.

16. The method of claim 9 wherein the image is acquired during a fixed point of a subsequent diastole period of the cardiac cycle.

17. The method of claim 16 wherein the fixed point of a subsequent diastole period of the cardiac cycle is the midpoint of a subsequent diastole period.

18. The method of claim 9 wherein said the image is acquired in a specific sub-phase of a subsequent diastole period of the cardiac cycle.

* * * * *